(12) United States Patent
Viazis

(10) Patent No.: US 10,117,728 B2
(45) Date of Patent: Nov. 6, 2018

(54) METHOD AND APPARATUS FOR TREATING ORTHODONTITIS

(71) Applicant: ORALECT LICENSING, LTD, Plano, TX (US)

(72) Inventor: Anthony D. Viazis, Dallas, TX (US)

(73) Assignee: ORALECT LICENSING, LTD., Dallas, TX (US)

( * ) Notice: Subject to any disclaimer, the term of this patent is extended or adjusted under 35 U.S.C. 154(b) by 353 days.

(21) Appl. No.: 14/528,319

(22) Filed: Oct. 30, 2014

(65) Prior Publication Data
US 2016/0120616 A1    May 5, 2016

(51) Int. Cl.
| | | |
|---|---|---|
| *A61C 3/00* | (2006.01) | |
| *A61C 7/14* | (2006.01) | |
| *A61C 7/20* | (2006.01) | |
| *A61C 7/12* | (2006.01) | |
| *A61C 7/00* | (2006.01) | |

(52) U.S. Cl.
CPC .............. *A61C 7/148* (2013.01); *A61C 7/12* (2013.01); *A61C 7/14* (2013.01); *A61C 7/20* (2013.01); *A61C 2007/004* (2013.01)

(58) Field of Classification Search
CPC .... A61C 7/20; A61C 7/12; A61C 7/14; A61C 7/148
USPC .................................................. 433/8, 10, 24
See application file for complete search history.

(56) References Cited

U.S. PATENT DOCUMENTS

| | | | | | |
|---|---|---|---|---|---|
| 4,386,908 | A | * | 6/1983 | Kurz .................... | A61C 7/145 433/8 |
| 4,582,487 | A | * | 4/1986 | Creekmore ........... | A61C 7/145 433/8 |
| 4,917,602 | A | * | 4/1990 | Broussard ............. | A61C 7/12 433/8 |
| 5,037,297 | A | * | 8/1991 | Lerner .................. | A61C 7/287 433/14 |
| 5,161,969 | A | * | 11/1992 | Pospisil ................ | A61C 7/12 433/10 |
| 5,302,116 | A | * | 4/1994 | Viazis ................... | A61C 7/12 433/10 |
| 5,380,197 | A | * | 1/1995 | Hanson ................ | A61C 7/303 433/18 |
| D367,116 | S | * | 2/1996 | Viazis ................... | A61C 7/12 D24/180 |

(Continued)

*Primary Examiner* — Nicholas Lucchesi
(74) *Attorney, Agent, or Firm* — Jeffrey G. Degenfelder; Carstens & Cahoon, LLP.

(57) ABSTRACT

A method for treating orthodontitis (i.e., gingivitis caused by malpositioned teeth). The process includes evaluating improper morphologies of alveolar bone in the horizontal dimension (i.e., orthodontosis) caused by displaced root(s) of a tooth, uprighting the root of the malpositioned tooth utilizing an orthodontic bracket system thereby causing the alveolar bone to be restored, which in-turn alleviates the orthodontitis. An orthodontic bracket is provided for use with an arch wire to apply corrective forces to a tooth. The bracket includes a vertical member having a slot formed therein for receiving the arch wire and a wide base horizontal member connected to the vertical member. The vertical member is positioned gingivally with respect to the horizontal member. The horizontal member includes opposing first and second ends that extend away from the vertical member and define a pair of spaced-apart wire engaging points engageable with the arch wire during treatment.

19 Claims, 12 Drawing Sheets

(56) References Cited

U.S. PATENT DOCUMENTS

| | | | | |
|---|---|---|---|---|
| 6,394,798 B1* | 5/2002 | Huff | ................... | A61C 7/14 |
| | | | | 433/10 |
| 8,251,696 B2* | 8/2012 | Rodriguez | ............ | A61C 7/287 |
| | | | | 433/10 |
| 8,376,739 B2* | 2/2013 | Dupray | ................ | A61C 7/143 |
| | | | | 433/10 |
| 2010/0092905 A1* | 4/2010 | Martin | ................. | A61C 7/00 |
| | | | | 433/18 |
| 2010/0178628 A1* | 7/2010 | Kim | ..................... | A61C 7/12 |
| | | | | 433/10 |
| 2012/0214121 A1* | 8/2012 | Greenberg | .......... | A61B 5/0088 |
| | | | | 433/24 |
| 2015/0343208 A1* | 12/2015 | Davidovitch | ........... | A61C 7/00 |
| | | | | 433/6 |

\* cited by examiner

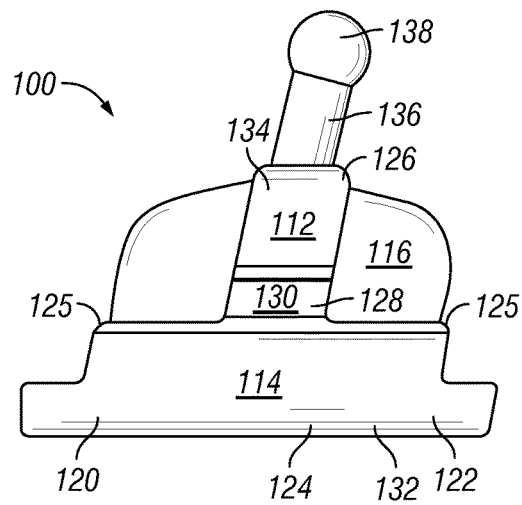
*FIG. 9*
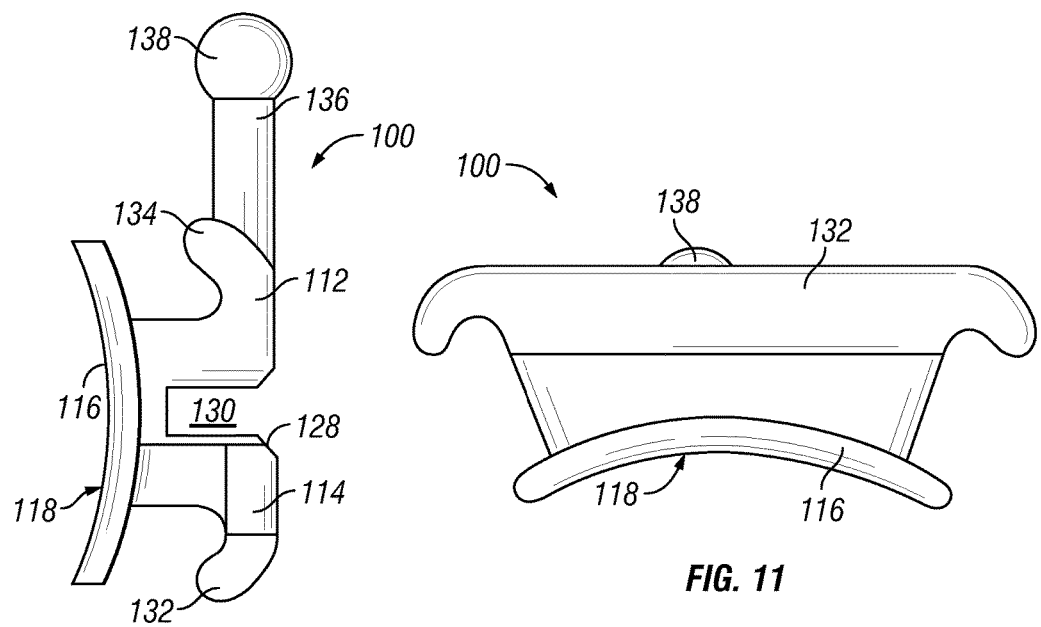
*FIG. 10*
*FIG. 11*

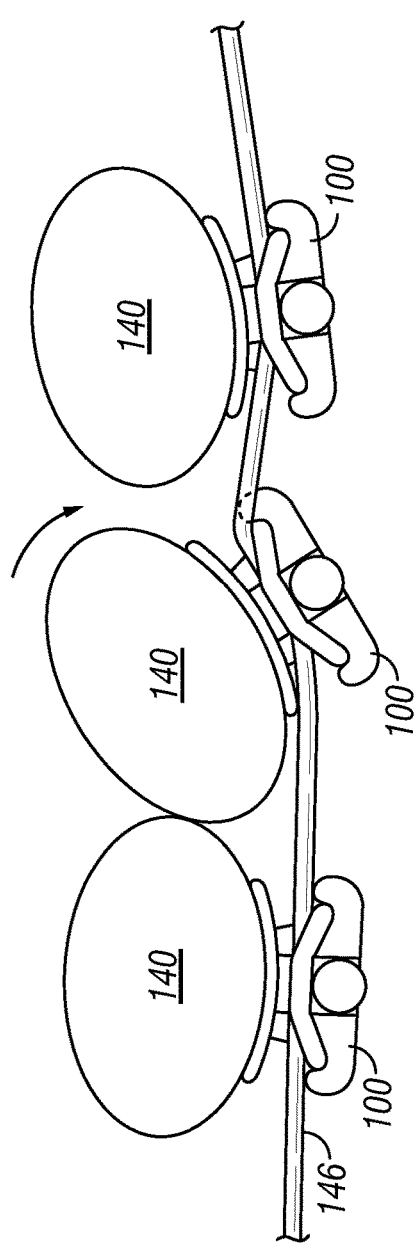
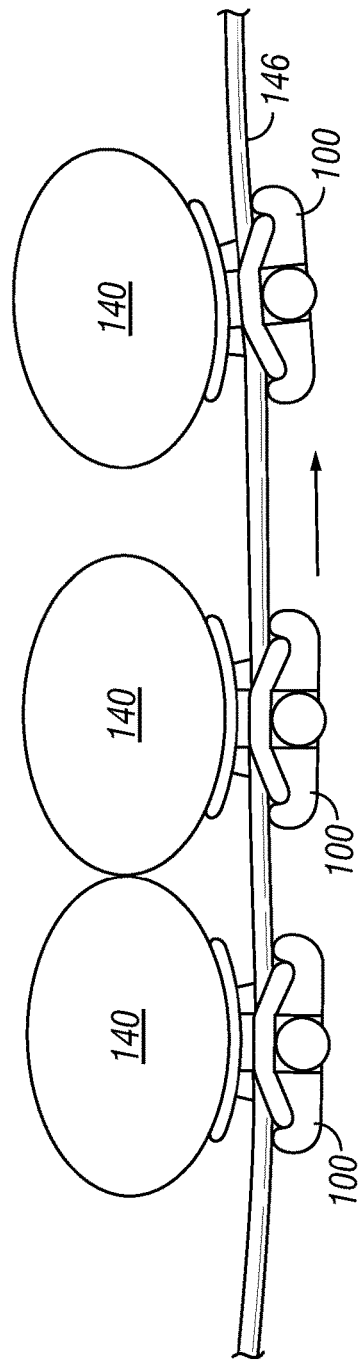
FIG. 12B
FIG. 12C

METHOD AND APPARATUS FOR TREATING ORTHODONTITIS

BACKGROUND OF THE INVENTION

1. Technical Field of the Invention

This invention relates generally to orthodontics and orthodontic appliances and, more particularly, to the characterization and treatment of malocclusions and to orthodontic brackets used in the treatment of orthodontitis, i.e., gingivitis caused by malpositioned teeth.

2. Description of the Related Art

Gingivitis is an inflammatory process affecting the soft tissues surrounding the teeth. Gingivitis describes inflammation of the gingivae, characterized by swelling, redness, influx of inflammatory cells, edema in the tissue, change of normal contours, and bleeding. Gingivitis is typically diagnosed when the gingiva appears red and puffy, loses its stippling, and bleeds spontaneously or on probing. Plaque-induced gingivitis is reversible by scaling and cleaning the teeth. However, if the bacterial plaque is not removed, the gingivitis progresses through the stages of chronic gingivitis and chronic periodontitis to chronic destructive periodontitis. Gingival pockets from tissue swelling and loss of attachment not involving bone are usually present. Gingivitis may be either acute or chronic, with emissions and exacerbations. General causes include hypovitaminosis, blood dyscrasias, allergic reactions, endocrine disturbances, such as diabetes mellitus, drugs such as diphenylhydantoin or the heavy metals, chronic debilitating disease or local factors such as dental calculus or plaque, food impaction, or faulty dental restorations and dental hygiene. The inhibition, prevention and treatment of gingivitis has varied little over the past two decades and consists primarily of establishing good oral hygiene and maintaining a periodontal environment that is easily kept clean by the patient. See, e.g., PCT Pub. Nos. WO 1996/009834 A1 and WO 1988/003021 A3; U.S. Pat. Nos. 3,577,520, 3,911,133 and 4,243,670; and European Pat. Pub. Nos. 0 345 039. Such topical and medicinal therapies are not only long and expensive, but never truly end. Moreover, such therapies are typically directed only at the resulting symptoms of gingivitis without addressing the underlying cause(s). Clearly, new modes of therapy are needed to substitute and augment current prophylaxis procedures.

Generally, treatment planning of orthodontic care is based primarily on the premise of improvements of function, dental and facial esthetics and general dental health. Recent clinical observation and experience has suggested that a common underlying cause of gingivitis is misaligned teeth or malocclusions. However, to date, a link between malocclusions and periodontal condition remains unclear and controversial. For example, the findings of one literature review on the impact of malocclusions and orthodontic treatment of periodontal health does not show a clear correlation (see Van Gastel, et al., Aust Orthod J 23(2): 121-129). Furthermore, a 2008 systematic review by Gray and McIntyre (see J. Orthod. 2008; 35: 262-9) shows a positive association of orthodontic care and periodontal health by quantifying the impact of orthodontic oral health promotion (OHP) which produced a reduction in plaque with an improvement in gingival health.

Nonetheless, at the outset it should be understood that a critical prerequisite for any effective orthodontic treatment is a proper understanding and classification of malocclusion. For without a proper understanding and classification of the problem (i.e., misaligned teeth), the effectiveness of any orthodontic treatment cannot be maximized. Currently there are several classifications of malocclusion, which include classic qualitative methods such as Dr. Edward Angle's classification and more contemporary quantitative methods and indices such as Peer assessment rating (PAR) and Index of orthodontic treatment need (IOTN). Considered by many to be the father of modern orthodontics, Dr. Angle was the first to classify malocclusion. First developed in the late 19$^{th}$ Century, Angle's classification system has remarkably endured the test of time and continues to be utilized as the main language of malocclusion among orthodontic specialists.

As shown in FIG. 1a, in accordance with the Angle's classification system, a proper or ideal occlusion has a molar relationship where the mesiobuccal cusp of the upper first molar 2 is aligned with the buccal groove of the mandibular first molar 4. The teeth should all fit on a line of occlusion which, in the upper arch, is a smooth curve through the central fossae of the posterior teeth and cingulum of the canines and incisors, and in the lower arch, is a smooth curve through the buccal cusps of the posterior teeth and incisal edges of the anterior teeth. Other factors for a proper occlusion include that all the teeth of the upper jaw are slightly over the lower teeth in the horizontal dimension (i.e., an overjet). A proper overjet 3 is from 2 to 3 mm. The teeth are formed in a nice uniform arch and there are no tooth rotations. Currently, dental professionals strive to obtain a proper occlusion when treating a malocclusion. Any variations from the proper occlusion results in malocclusion types, which are divided into three classes:

Class I Malocclusion: While the molar relationship of the occlusion is proper or normal, the other teeth have problems like spacing, crowding, over or under eruption, etc.

Class II Malocclusion—Overbite (FIG. 1b): A molar relationship where the mesiobuccal cusp of the upper first molar 2 is not aligned with the mesiobuccal groove of the lower first molar 4. Instead it is anterior to it. Any amount of overjet 3 more than 3 mm is not within normal limits.

Class III Malocclusion—Underbite (FIG. 1c): A molar relationship where the upper molars 2 are aligned posteriorly to the mesiobuccal groove and the lower front (anterior) incisor teeth 6 are farther forward than the upper incisors 7, resulting in an anterior crossbite. The mesiobuccal cusp of the maxillary first molar 2 lies posteriorly to the mesiobuccal groove of the mandibular first molar 4. It is usually seen when the lower front teeth 6 are more prominent than the upper front teeth 7.

Yet, there continues to be an emerging body of literature that exposes the lack of evidence for this conventional classification of malocclusion. For example, one study showed poor diagnostic inter-provider reliability (see Gravely J F, Johnson D B. Angle's classification of malocclusion: an assessment of reliability. Br J Orthod 1974; 1:79-86) while another survey study among 34 chairpersons of Orthodontics Departments in the U.S. showed that fewer than 65% were in agreement on the meaning of a Class II sub-division. (see Siegel N A. A matter of class: interpreting sub-division in a malocclusion. Am J Orthod Dentofac Orthop 2002; 122: 582-586)

An editorial published in the American Journal of Orthodontics in 2009 stated that, although the concept of ideal occlusion has taken precedence as the ultimate goal in clinical orthodontics for some 110 years and serves as an adopted arbitrary method convention and clinical gold standard, it has no verifiable scientific validity, and that no one has yet demonstrated that ideal occlusion provides significant benefits in oral or general health, or that it significantly improves oral function. (see Ackerman, James and William Proffit: A not-so-tender trap, Am J Orthod Dentofacial Orthop 2009; 136:619-620)

A 2002 article also questioned the arbitrary nature of this classification that suggests a change in a stable, functional mandibular position in order to achieve a morphologic occlusion that conforms to an arbitrary ideal. (see Rinchuse, Daniel and Donald Rinchuse: Orthodontics justified as a profession, Am J Orthod Dentofacial Orthop 121:93-6, 2002) Indeed, the Angle Classification system is based upon a positioning of the teeth, which, it is estimated, teeth normally maintain for less than 20 minutes per day. Moreover, the arbitrary esthetic ideal of the Angle Classification system is thought to be based upon a euro-centric facial structure, which is structurally distinguishable from and unsuitable for the facial structure of other racial and ethnic groups.

Thus, the Angle Classification system inherently includes several drawbacks that hamper its ability to correctly define a proper occlusion or to diagnose malocclusions across a wide variety of patients from different and diverse racial and ethnic groups. Clearly, a new classification system is needed to more accurately define a proper occlusion and diagnose malocclusion. Moreover, a new classification system is needed to diagnose and treat patients based upon their individual genetic and morphologic appearance rather than an arbitrary ideal. Once the malocclusion has been correctly identified, treatment solutions can be implemented more effectively.

SUMMARY OF THE INVENTION

The present invention overcomes many of the disadvantages of prior art by treating gingivitis caused by malpositioned teeth (i.e., orthodontitis). The process includes evaluating deficiencies of the alveolar bone in the horizontal dimension caused by displaced root(s) of a tooth; uprighting the root of a malpositioned tooth utilizing an orthodontic bracket system thereby causing the alveolar bone to be restored, which in-turn alleviates orthodontitis.

The present treatment of orthodontitis is directed to an orthodontic bracket for use with an arch wire for applying corrective forces to a tooth, which in turn remedies deficiencies of the alveolar bone. In a preferred embodiment, the orthodontic bracket includes a vertical member connected to a horizontal member. The vertical member is positioned gingivally with respect to the horizontal member and includes a slot therein for receiving the arch wire. The horizontal member includes opposing first and second ends that extend away from the vertical member and define a pair of spaced-apart wire engaging points engageable with the arch wire as the tooth rotates during treatment.

Brackets constructed in accordance with the preferred embodiment of the present invention have small arch wire slots and large inter-bracket distances. Consequently, the arch wire span between brackets is large, enhancing the flexibility of the arch wire and enabling greater control over the forces exerted by the arch wire. The small slot size also reduces friction between the arch wire and the slot during tooth movement. Furthermore, the brackets provide excellent rotational, torque and tip control because of their general triangular shape with spaced apart wire engaging points.

Orthodontic brackets in accordance with the invention are particularly suited for the tooth to which they are applied. In this regard, applicant's customized triangular shaped bracket is provided with a horizontal member of a width of between 60-90% of the width of the tooth, preferably between 65-85%. The wide based triangular shaped bracket provides an increased moment to improve tooth control with a large inter-bracket slot distance to improve arch wire performance. The bracket is provided with rounded corners and edges to reduce irritation and increase wearing comfort.

BRIEF DESCRIPTION OF THE DRAWINGS

A more complete understanding of the method and apparatus of the present invention may be had by reference to the following detailed description when taken in conjunction with the accompanying drawings, wherein:

FIG. 9 is a front view of a bracket constructed in accordance with the present invention;

FIG. 10 is a side view of the bracket shown in FIG. 9;

FIG. 11 is a bottom view of the bracket shown in FIGS. 9 and 10;

FIG. 12B is a plan view illustrating corrective rotational movement of a tooth;

FIG. 12C is a plan view illustrating corrective sideward movement of a tooth.

Figure 1A:
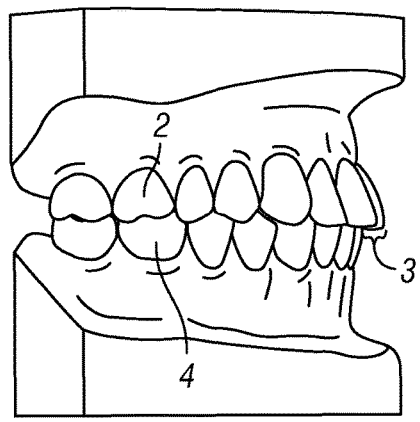
FIG. 1A depicts the side view of a proper occlusion in accordance with the prior art Angle classification system.
Figure 1B:
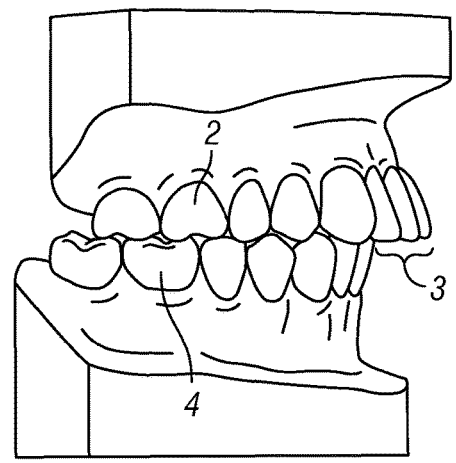
FIG. 1B depicts the side view of a Class II Malocclusion in accordance with the prior art Angle classification system.
Figure 1C:
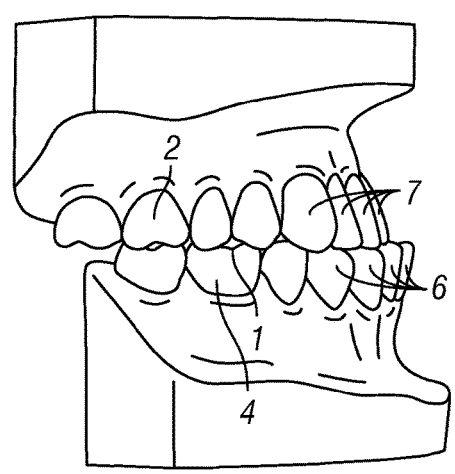
FIG. 1C depicts the side view of a Class III Malocclusion in accordance with the prior art Angle classification system.

Where used in the various figures of the drawing, the same numerals designate the same or similar parts. Furthermore, when the terms "top," "bottom," "first," "second," "upper," "lower," "height," "width," "length," "end," "side," "horizontal," "vertical," and similar terms are used herein, it should be understood that these terms have reference only to the structure shown in the drawing and are utilized only to facilitate describing the invention.

All figures are drawn for ease of explanation of the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

DETAILED DESCRIPTION OF THE INVENTION

The Angle Classification system is based primarily upon the position and alignment of the teeth in a biting position. However, humans bite down and chew, more or less, for only about 15 minutes a day. This prompts the question, why should a dentist base his/her diagnosis of a patient's malpositioned teeth on such a transitory occlusion? Clinical observation and experience has resulted in the establishment of a new classification for malpositioned teeth based upon the clinical morphology, appearance and contour of the alveolar bone and ridge. The proposed classification of malpositioned teeth by evaluating the alveolar bone and roots in the horizontal dimension is consistent with differences found in the microbial composition of subgingival plaque of malpositioned vs. non-malpositioned teeth.

While several factors contribute to the microbial colonization of dental plaque including pH, temperature and osmotic pressure, physical barriers to self-cleansing caused by malpositioned teeth facilitate the accumulation of plaque and its microbial constituents. One study concluded that compared to non-malpositioned anterior dentition in adults, malpositioned anterior dentition exhibited greater plaque accumulation, a greater number of periodontopathogens present in sub gingival plaque with a significantly more common presence of Fusobacterium species, Capnocytophaga species, C rectus and P micros. (see Chung et al., Int J Adult Orthodon Orthognath Surg 15(4): 321-330) In addition, another study examined levels of multiple periodontal pathogens and concluded that orthodontic treatment had a positive effect post treatment and was protective for four of the pathogens, namely Eikenella corrodens, Fusobacterium nucleatum, Treponema denticola, and Campylobacter rectus. (see Thornberg et al., Am J Orthod Dentofacial Orthop 135(1): 95-98) The proposed classification is a paradigm shift from the traditional orthodontic thinking and more in line with the current accepted theories found in the periodontal literature and the specialty of periodontics.

The alveolar bone is the thickened ridge of bone that contains the tooth sockets on bones that hold teeth. The tooth-bearing bones include the upper palate of the mouth or maxillae and the lower jaw or mandible. The new classification is based upon an evaluation of orthodontosis present in a patient's teeth. Orthodontosis is defined as a non-inflammatory improper morphology of alveolar bone in the horizontal dimension caused by the displaced root(s) of the tooth, typically palatally or lingually. This improper morphology typically demonstrates itself as either a deficiency or an excess of the alveolar bone. The deficiency or excess of alveolar bone results in excess soft tissue manifestation and chronic inflammation called orthodontitis or gingivitis caused by malpositioned teeth. It has been found that once the root of a malpositioned tooth is uprighted or corrected, the alveolar bone is restored, which in-turn alleviates the orthodontitis (i.e., gingivitis caused by malpositioned teeth).

The proposed orthodontic diagnosis system of the present invention, based on the morphology of the alveolar bone, accepts the patient's natural dentition within its own hard tissue and soft tissue substrate. Therefore, patients are simply diagnosed and treated accordingly based on their own individual genetic and morphologic appearance and not based on arbitrary ideals. As a result of the proposed new concept, people's faces all over the world are accepted de facto and are not be subject to alteration from extractions that would mutilate the natural facial protrusion. In accordance with the classification and diagnosis system of the present invention, natural facial protrusions are accepted as normal and natural for each specific individual. If an individual wishes any facial alteration of their alveolar appearance beyond a straight smile, then periodontal/oral maxillofacial and or plastic surgery may be in order.

Figure 2A:
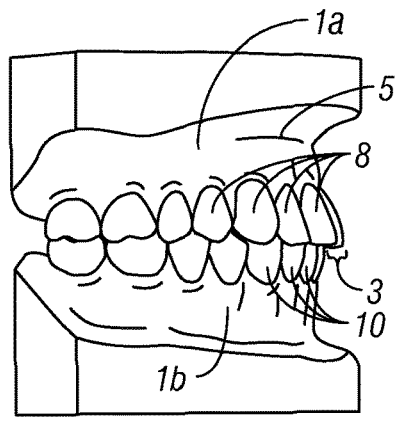
FIG. 2A depicts a side view of a proper occlusion in accordance with the classification system of the present invention.

A proper or ideal occlusion in accordance with the classification system of the present invention is shown in FIG. 2A. While a proper or ideal occlusion of the present invention appears to look generally similar to that of the Angle classification system, the focus is on evaluating the development of the alveolar bones 1a, 1b. Factors for a proper occlusion include that all the teeth of the upper jaw 5 are formed slightly over the lower teeth in the horizontal dimension (i.e., an overjet 3). A proper overjet 3 is from 2 to 3 mm. The teeth are in a nice uniform arch and there are no tooth rotations. However, instead of focusing on the alignment of the molars, the present classification system analyzes the alveolar bones 1a, 1b above and below the upper 8 and lower anterior teeth 10, respectively.

Orthodontosis is an improper morphology of the alveolar bone in the horizontal dimension caused by the absence of the erupted root in that position that results in orthodontitis (i.e., gingivitis caused by bad tooth position). Orthodontosis arises in three contexts: localized, premaxillary and mandibular. At the outset, it should be noted that the classifications are descriptive, morphologic definitions and not ones of disease. The actual disease is disruption of eruption that results in displaced roots and inadequate or improper alveolar bone formation leading to boney defects. Thus, the method of the present invention treats defects in the alveolar bone in order to straighten teeth properly. The orthodontic diagnosis in accordance with the present invention is no longer derived from the occlusion or malocclusion but from the condition of the alveolar bone.

In accordance with the methods of the present invention, orthodontics means root parallelism with the root apex pointing slightly towards the distal. Parallel roots can handle the masseter muscles forces and minimize traumatic occlusion. The masseter muscles typically covers the corner area of the lower jaw. In accordance with the methods of the present invention the natural bite of a patient (i.e., from the second premolar back) leaves the molar bite alone and corrects the rest of the bite from the premolar forward.

Class A Malocclusion

Localized Orthodontosis—Localized Deficiency of the Alveolar Bone

Figure 3A:
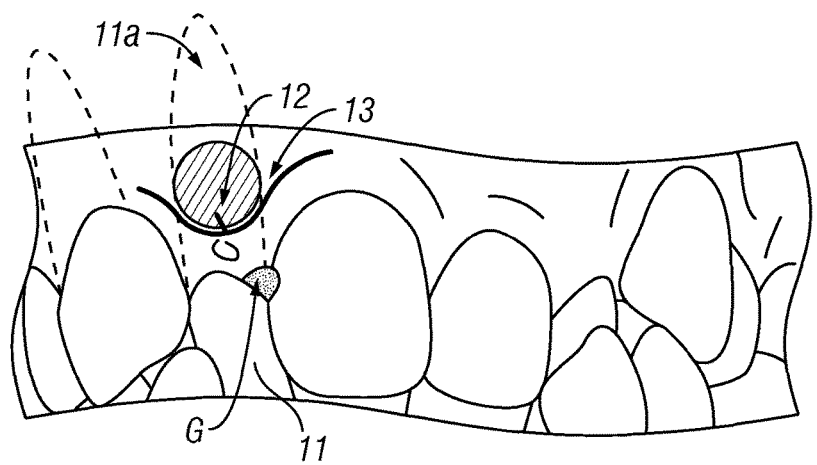
FIG. 3A depicts a frontal view of a Class A Malocclusion (i.e., localized orthodontosis) in accordance with the classification system of the present invention.
Figure 3B:
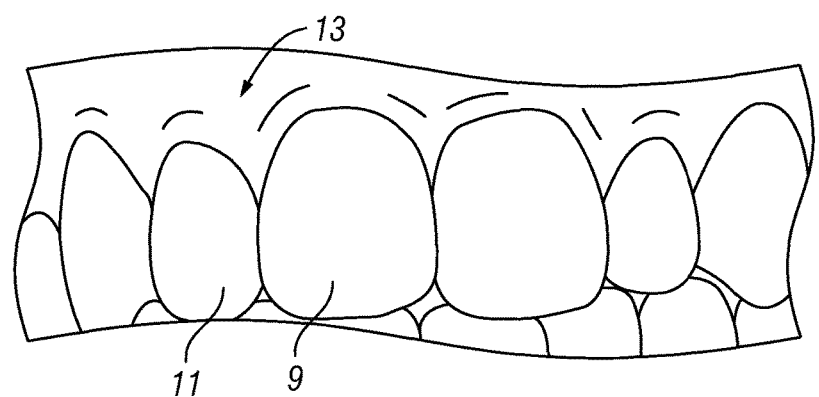
FIG. 3B depicts the frontal view of the Class A Malocclusion (i.e., localized orthodontosis) shown in FIG. 3A corrected to a proper occlusion utilizing the method of the present invention.
Figure 4:
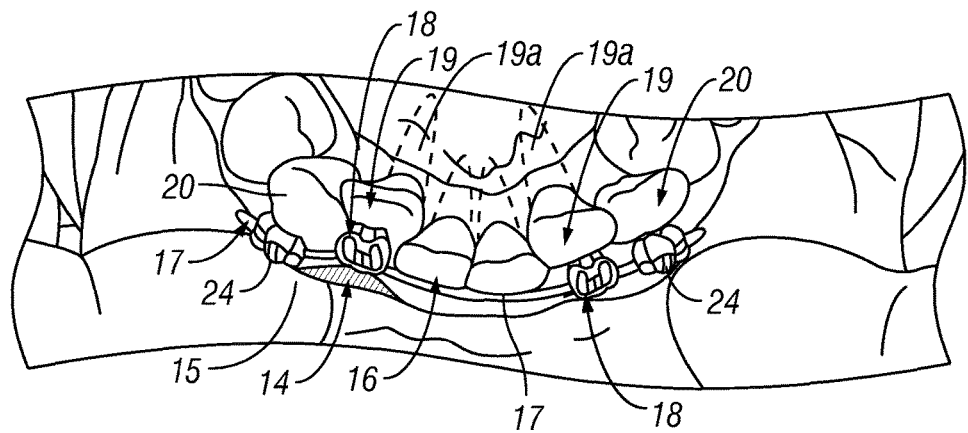
FIG. 4 depicts a perspective view of the treatment of another example of a Class A Malocclusion (i.e., localized orthodontosis) in accordance with the method of the present invention.
Figure 5A:
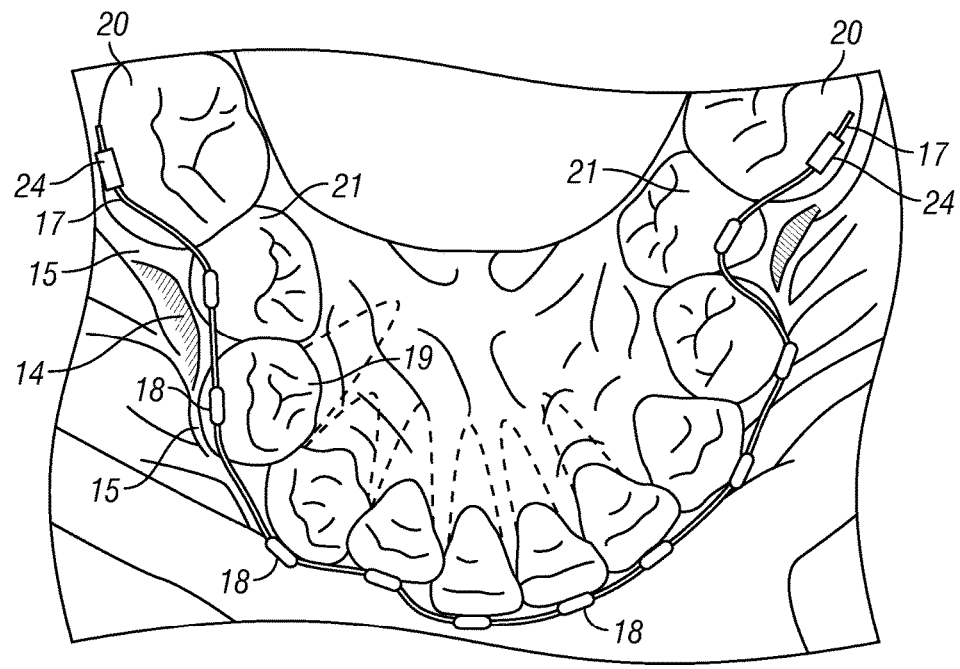
FIG. 5A depicts a occlusal view of the mandible for another example of a Class A Malocclusion (i.e., localized orthodontosis) in accordance with the classification system of the present invention, which exhibits deficiencies of the alveolar bone morphology by the first premolars.

This condition typically has an overbite/overjet relation of 2-3 mm which is adequate for anterior guidance. Localized orthodontosis is the deficiency of the alveolar bone at a specific location of the alveolar bone or tooth in the horizontal dimension caused by the displaced root(s) of the tooth, typically palatally or lingually. This deficiency of the alveolar bone results in excess soft tissue and chronic inflammation called orthodontitis. For example, FIGS. 3A, 4 and 5A depict specific examples of Class A Malocclusions or localized orthodontosis. FIG. 3A depicts a situation where the upper right lateral incisor root 11a has improperly erupted more palatally. Thus, the alveolar bone 13 above it has formed more palatally as well, creating a depression 12 (i.e., deficiency) in the outline of the alveolar bone 13 above the root 11. The soft tissue (i.e., gums) around the deficiency 12 of alveolar bone 13 is more susceptible to trapping food in its creases due to its deflated surface. This results in gingivitis G (i.e., orthodontitis) as the patient cannot clean the area effectively. In contrast, FIG. 3B depicts the frontal view of the Class A Malocclusion (i.e., localized orthodontosis) shown in FIG. 3A corrected to a proper occlusion utilizing the method of the present invention. The method of the present invention induces movement of the root 11a which in turn causes orthoeruption on the tooth root 11a which serves to restore the alveolar bone 13. As shown in FIG. 3B, the alveolar bone 13 is restored on the root 11a of the upper right lateral incisor tooth 11, which has been moved into an upright position from orthoeruption.

Likewise, FIG. 4 depicts a localized orthodontosis situation where the lower alveolar bone 15 appears to be concave 14 (i.e., deficient) by the lateral incisors 19 instead of convex (i.e., in front of) as with the central incisors 16. As will be explained in greater detail below, orthodontic appliances or brackets 18 are attached to the misaligned lateral incisors 19. A wire 17 configured in the slot of each bracket 18 is used to torque the roots of the lateral incisors 19 causing the alveolar bone 15 above these roots to remodel more labially, restoring the bone morphology as the tooth is straightened. Preferably, the slot of each bracket 18 has a rectangular or square cross section and the wire 17 has a complementary cross section.

Figure 5B:
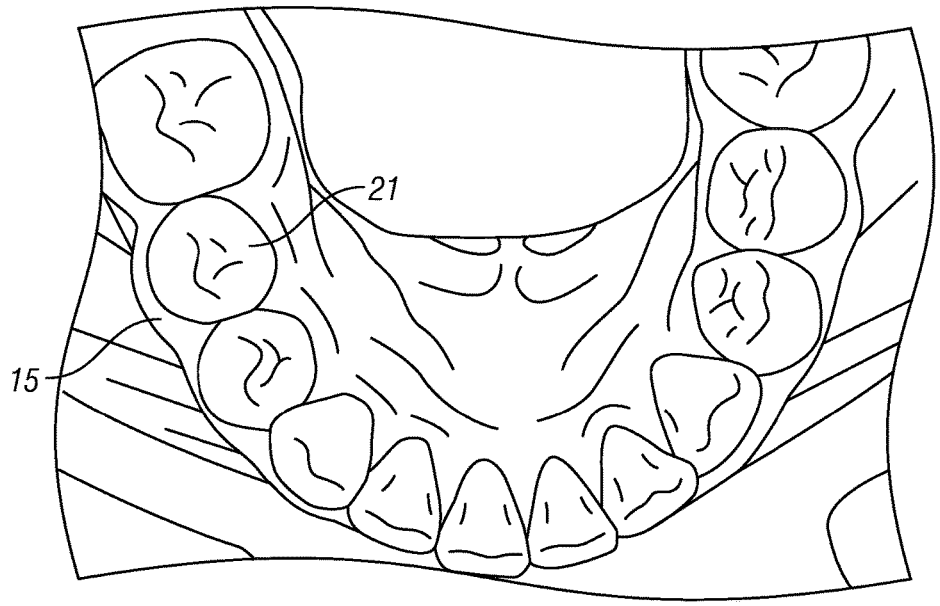
FIG. 5B depicts an occlusal view of the mandible for the Class A Malocclusion (i.e., localized orthodontosis) shown in FIG. 5A, corrected to a proper occlusion utilizing the method of the present invention.

Similarly, FIGS. 5A-5B depict another occurrence of localized orthodontosis where the alveolar bone 15 exhibits a concave appearance or deficiency 14 from the improperly erupted lower first premolars 21 more lingually. As shown in FIG. 5A, and will be explained in greater detail, the method of the present invention uses orthodontic appliances or brackets 18 attached to certain misaligned teeth to cause root movement utilizing a single wire 17 (preferably having a rectangular or square cross section), as opposed to tilting the crown of the tooth as done with conventional orthodontic braces using a series of round wires. The movement of the roots causes orthoeruption on the tooth roots which serves to restore the alveolar bone 15. Thus, as shown in FIG. 5B, the alveolar bone 15 is restored on the root of the premolar tooth 21 which was moved into position from orthoeruption.

Class B Malocclusion

Premaxillary Orthodontosis—Deficiency of the Alveolar Bone in the Premaxilla

Figure 2B:
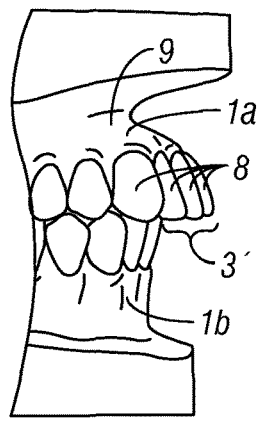
FIGS. 2B and 2C depict perspective side views of Class B Malocclusions (i.e., premaxillary orthodontosis) in accordance with the classification system of the present invention.
Figure 2C:
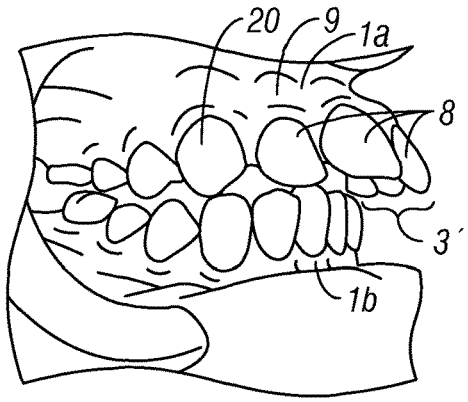

As depicted in FIGS. 2B-2C, these types of cases typically demonstrate flared upper anterior teeth 8 and a premaxilla 9 (defined as the upper jaw from canine to canine e.g., 20) that is underdeveloped as the roots of the upper anterior teeth 8 have not erupted to their full upright potential. As a result, the overbite/overjet 3' relation is excessive. As will be explained in greater detail, the method of the present invention utilizes a novel orthodontic bracket and arch wire system to upright the roots of the misaligned teeth from the beginning of treatment causing the restoration of the alveolar bone 1 about the roots of the teeth and consequently eliminating the depression in the gums. By restoring the alveolar bone 1, the premaxillary orthodontosis is alleviated resulting in the elimination of a primary cause of the orthodontitis. The method of the present invention may also include an upper interproximal enamel reduction of the width of the upper teeth, molar to molar, to assist in alleviating this condition and restoring the alveolar bone to a proper level by creating spaces between the upper teeth and subsequently closing these spaces by uprighting the upper teeth into these spaces. If the patient also demonstrates mandibular retrognathia, then a surgical procedure may also be indicated.

Class C Malocclusion

Mandibular Orthodontosis—Excess Alveolar Bone Inward Tilt

Figure 2D:
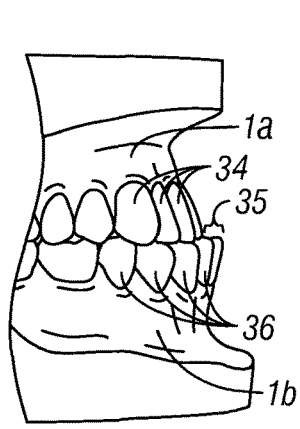
FIGS. 2D and 2E depict a side and front view, respectfully, of a Class C Malocclusion (i.e., mandibular orthodontosis) in accordance with the classification system of the present invention.
Figure 2E:
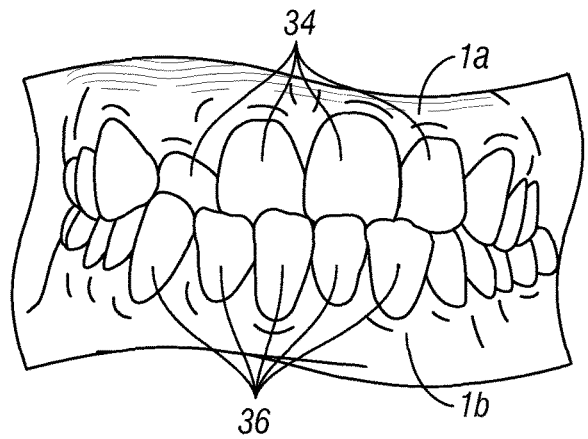

As depicted in FIGS. 2D-2E, these types of cases typically demonstrate minimal overbite/overjet with retroclined lower incisors 36 or negative overjet 35 (i.e., underbite). Apart from a slight maxillary deficiency, these cases show excess mandibular alveolar bone inward tilt with retroclined lower teeth 36 (see also, e.g., FIG. 8A).

Figure 8A:
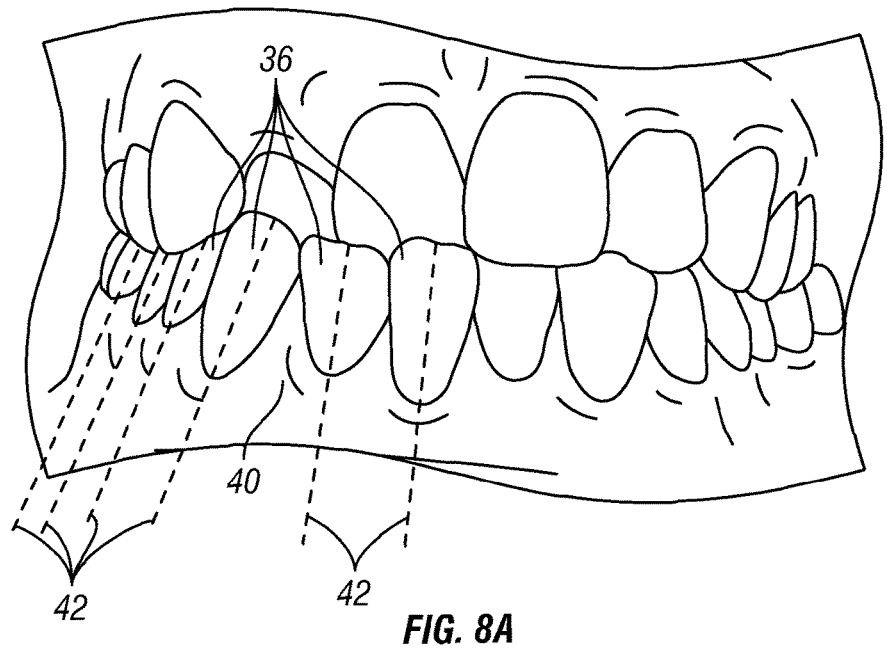
FIG. 8A depicts a frontal view of a Class C Malocclusion (i.e., mandibular orthodontosis) in accordance with the classification system of the present invention, that exhibits excessive inward tilt of the alveolar bone morphology by the lower right cuspid and premolar areas.
Figure 8B:
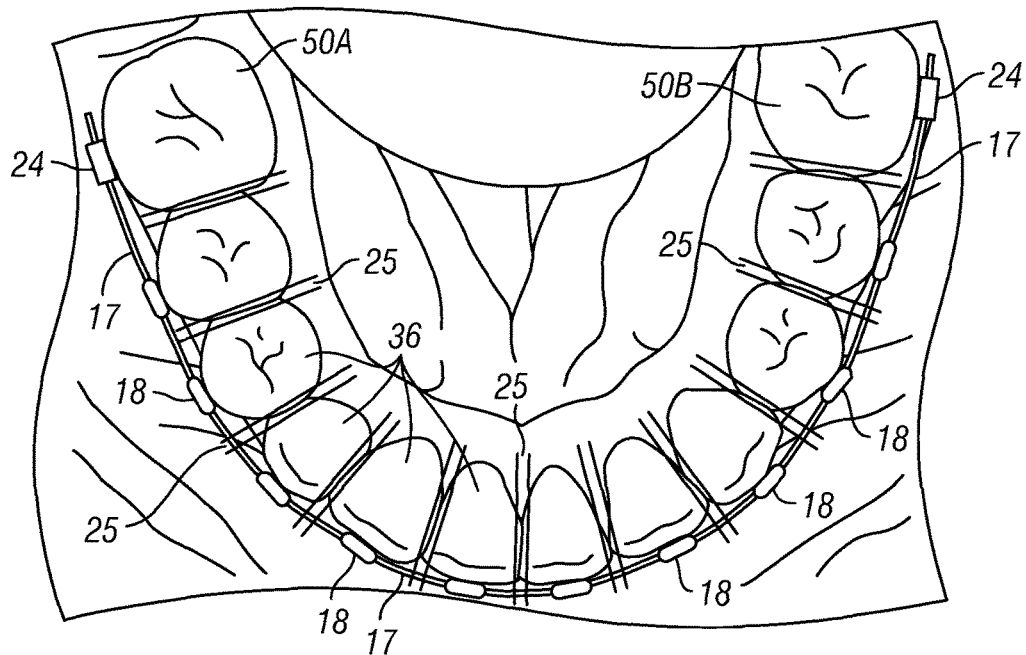
FIG. 8B depicts an occlusal view of the mandible for the Class C Malocclusion (i.e., mandibular orthodontosis) shown in FIG. 8A, showing the placement of brackets and spaces created in accordance with the method of the present invention.

For example, as shown in FIG. 8B and will be explained subsequently in greater detail, the method of the present invention uses the lower interproximal enamel reduction of the width of the lower teeth, molar to molar, to alleviate this condition for up to three lower anterior teeth in an underbite relation. The alveolar bone is restored to a more proper morphology (See FIG. 8B) by creating spaces 25 between the lower teeth (e.g., 36) and subsequently closing these spaces 25 by uprighting the lower teeth (e.g., 36) into these spaces 25. If more teeth are in anterior crossbite then a surgical procedure may also be indicated.

The Concept of Orthoeruption.

The formation of the human tooth represents a complex participation of various cell/tissue types involving interactions between ectoderm and neural-crest-derived mesenchyme. A process of differentiation ultimately gives way to the development of a functional unit, which includes the tooth and surrounding periodontal tissue (i.e., alveolar bone, periodontal ligament). The area between the alveolar bone and tooth cementum, which has been referred to as the tooth-bone interface (TBI), houses the soft tissue of the periodontal ligament in a developed and functional tooth. During the development of a tooth crown the TBI creates space for the developing tooth to grow while providing a soft tissue space for periodontal ligament formation during root development. While the TBI possesses an ostegenic potential it is essential that the space remain free from mineralization in order to prevent ankylosis of the developing tooth and root. This appears to involve the coordinated action of osteoclasts. The impaired function of osteoclasts in the adjacent tooth-bone interface would cause alveolar bone growth into the space, impaired development of the growing tooth germ and primary failure of eruption in humans. Therefore, the regulation of osteoclastogenesis plays a critical role by providing a clear path in bone for tooth eruption and root formation.

Eruption of a developing tooth crown begins with root development by the movement of the crown away from the point of initial root development after a force is initiated to move the tooth along a certain eruption path. Eruption requires the fulfillment of two criteria: 1) a force must be initiated to move a tooth along a certain eruption path; 2) the resorption or elimination of primary tooth roots. Many theories of eruptive movement have been proposed including force from cellular proliferation at the apex and variation in blood flow or pressure in the periodontal ligament.

About 20 years ago, a new theory was developed regarding orthodontic tooth movement after tooth eruption was completed (see U.S. Pat. No. 5,302,116). Uprighting the roots of malpositioned teeth from the beginning of orthodontic treatment led to the evolution of a new theory of orthodontic tooth movement after completion of tooth eruption. Based on generally accepted concepts of resorption from compression and bone formation by tension forces, it has been further realized that very light orthodontic forces may possibly be able to simulate bone remodeling around the area of displaced ("crooked") roots. This allows for the uprighting of displaced roots into a straight position as if the tooth erupted in that position initially, thus the term "orthoeruption". Orthoeruption results in the alveolar bone remodeling and restoration of the dental arch to its appropriate natural size and shape for each specific mouth.

Further research has demonstrated that orthodontic tooth movement (OTM) and accompanying bone remodeling processes are caused by varying changes in the stress/strain distribution in the periodontium caused by intra-alveolar movement of the roots. The mechanical stimulus provided by the moving roots translates into a biological response which is termed mechanotransduction. Commonly accepted theories of tissue reaction to orthodontic forces include: i) the pressure-tension theory which refers to the alteration in blood flow associated with pressure within periodontal ligament (PDL) causing activation of PDL cells and bone remodeling; and ii) the "bioelectric" theory which attributes tooth movement to changes in bone metabolism initiated with the deformation of alveolar bone and controlled by electrical signals. Other studies (see e.g., Orthod Craniofac Res 2009; 12:120-128) have shown that alveolar bone remodeling cannot be based the above referenced theories which contemplate simplified but generally accepted concepts of resorption from compression and bone formation by tension forces. Fundamentally, the process of tooth movement in an eruption path as well as theories of tissue reaction to orthodontic forces remains unclear.

Very light forces are needed to simulate the low force eruption stimuli that are needed to allow for bone remodeling around the displaced roots area of the alveolar bone and thus achieve correction of root position. Nonextraction therapy can now be achieved through bone "growth" remodeling as the alveolar bone reacts to a tooth erupting in its correct place in the arch. Thus, the root movement initiated at the onset of orthodontic treatment accordingly results in the orthoeruption of teeth.

The present treatment for orthodontitis is directed to an orthodontic bracket for use with an arch wire for applying corrective forces to a tooth, which in turn remedies improper morphology of the alveolar bone. In a preferred embodiment, the orthodontic bracket includes a vertical member connected to a horizontal member. The vertical member is positioned gingivally with respect to the horizontal member and includes a slot therein for receiving the arch wire. The horizontal member includes opposing first and second ends that extend away from the vertical member and define a pair of spaced-apart wire engaging points engageable with the arch wire as the tooth rotates during treatment. The bracket system of the present invention has been developed to specifically move the roots at the onset of orthodontic treatment with very light forces in order to simulate the low eruption stimuli needed to allow for bone remodeling around the displaced root area of the alveolar bone and thus achieve correction of root position. Reduction in the orthodontic force is achieved by significantly increasing the flexibility of the wire/bracket combination.

Conventional orthodontics consists of crown tipping with round wires during the $1^{st}$ year followed by a $2^{nd}$ year of root up righting with square wires. However, as the round wires tip the crowns they can "stress" the tip of the alveolar bone next to the CEJ and result in dehiscence or fenestration, etc. The orthodontic system of the present invention moves the apex of the root where the bone is thicker around it inducing a continuation of eruption by torqueing the roots.

FIGS. 9-11 illustrate the front, side and bottom views, respectively of a preferred embodiment of an orthodontic bracket generally indicated by reference character 100 in accordance with the present invention. The bracket 100 includes a vertical extending bar-like member or element 112, a horizontal extending bar-like member or element 114 and an underlying base portion 116.

As shown in FIGS. 10 and 11, the base portion 116 includes a tooth abutting surface 118, which is generally contoured to fit the outer shape of a tooth (not shown). The surface 118 is designed to receive adhesive material for bonding the bracket 100 to the tooth.

The horizontal bar 114 includes a first end 120 and an opposing second end 122 with a middle portion 124 therebetween. The ends 120 and 122 of the horizontal bar 114 extend horizontally and away from the middle portion 124, thereby forming two spaced apart wire engaging points 125 at upper corners of the horizontal bar 114.

The vertical bar 112 includes a first end portion 126 and an opposing second end portion 128. The second end portion 128 is connected to the horizontal bar 114 proximate the middle portion 124. The vertical and horizontal bars 112 and 114 may be joined together or formed integrally. When positioned on either upper or lower teeth, the vertical bar 112 will extend gingivally with respect to the horizontal bar 114 and generally in line with the axis of the tooth. (See FIG. 12A).

The vertical bar 112 has a height approximately equal to the width of the horizontal bar 114. The bars 112 and 114 may be perpendicular to each other. Alternately, as shown in FIG. 9, the angle between the bars 112 and 114 may be varied from 90° to accommodate the shape of particular teeth as will be discussed later. Preferably, the width of vertical bar 112 is approximately equal to that of a typical single wing bracket. Also, the length of the horizontal bar 114 is preferably customized for the tooth to which it is applied and is generally equal to or greater than the width of a typical twin bracket. More specifically, it has been found that for smaller teeth such as a lower center incisor, the horizontal bar is 3.2 mm. Similarly, for a cuspid or larger tooth, the horizontal bar is 6 mm. In this regard, it has been found that the horizontal bar should cover between 60-90% of the width of the tooth to which is it to be applied, the most preferred range being 65-85%.

An arch wire slot 130 is formed in the vertical bar 112 at the second end portion 128. The arch wire slot 130 is designed to receive an orthodontic arch wire (not shown) as will be further discussed with reference to FIGS. 12A and 13. Preferably, the arch wire slot 130 has a rectangular or square cross section and the arch wire 146 has a complementary cross section. As FIG. 10 indicates, the entrance to the slot 130 is chamfered at 128 to allow easy insertion of the arch wire. The slot 130 can be formed parallel to the horizontal bar 114 or at any angle thereto for enabling the arch wire to exert torque on the tooth. The slot 130 is slightly elevated from the horizontal bar 114 to avoid friction (See FIG. 13).

The horizontal bar 114 includes an edgewise tie-wing 132 projecting downwardly along the length of the horizontal bar 114. Similarly, the vertical bar 112 includes an upwardly projecting tie-wing 134 at the first end portion 126. The tie-wings 132 and 134 are designed to receive an o-ring, elastic chain, ligature wire or other securing device (not shown) as will be further discussed with reference to FIGS. 12A and 13.

An optional ball hook member 136 extends gingivally from the first end portion 126 of the vertical bar 112. The ball hook member 136 includes an enlarged ball portion 138 for facilitating the attachment of ligatures, elastics, coil springs or other force transmitting members (not shown). Although not shown, the ball hook member 136 may be replaced with a power arm or with other hook devices.

The bracket 100 may be formed of stainless steel material. Stainless steel, however, is only exemplary and can be changed as desired to ceramic, plastic or other suitable material.

As FIGS. 9-10 show, the edges and corners of the bracket 100 are generally rounded to reduce irritation and increase wearing comfort to the patient.

Figure 12A:
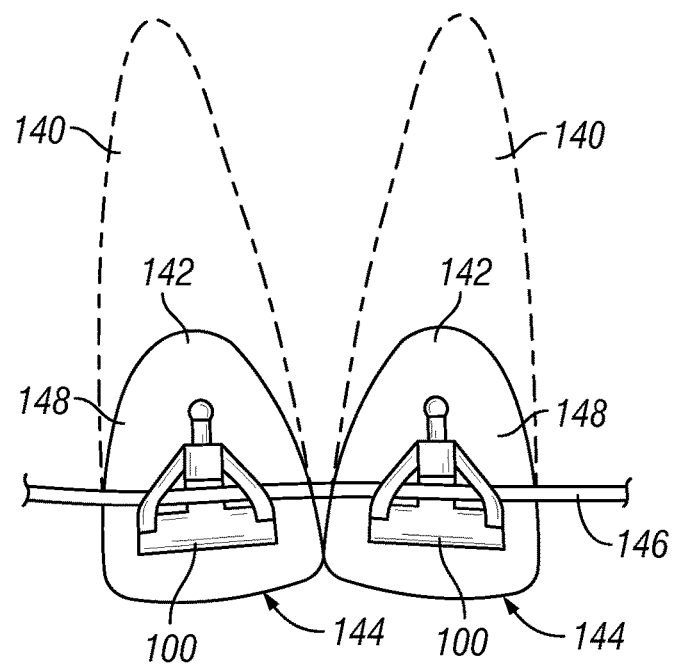
FIG. 12A illustrates the placement of two brackets on teeth.
Figure 13:
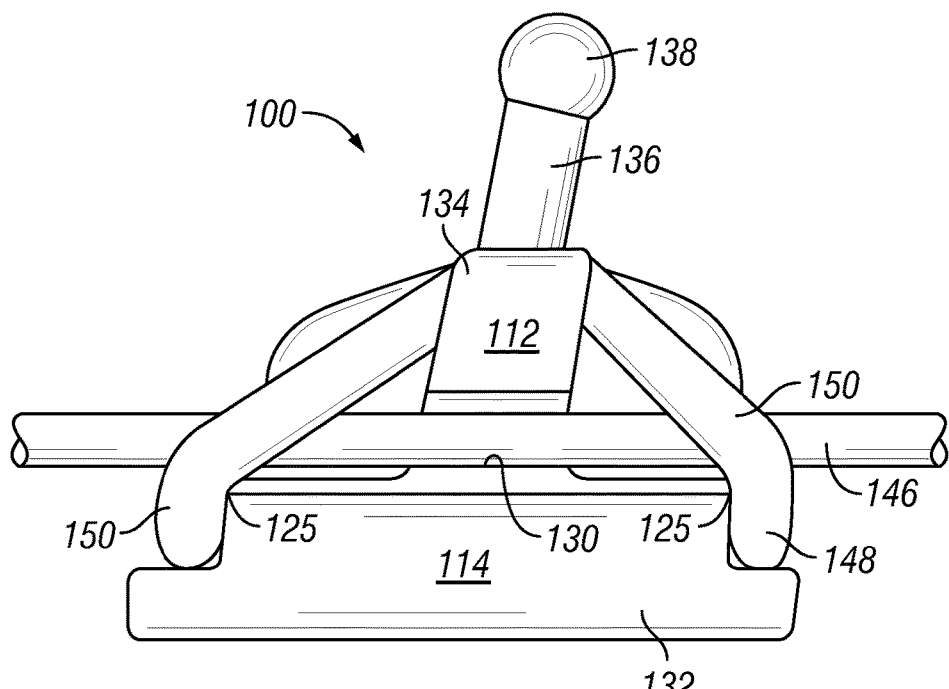
FIG. 13 is an enlarged view of one of the brackets shown in FIG. 12A.

FIG. 12A illustrates the placement of two brackets 100 on two upper teeth 140. FIG. 13 is an enlarged view of one of the brackets 100 shown in FIG. 12A. The teeth 140 include exposed crown portions 142 with occlusal surfaces 144 at the ends thereof. Each bracket 100 is generally centrally positioned on a crown portion 142 such that the vertical bar 112 and hook portion 136 are generally aligned with the long axis of the tooth 140 and the horizontal bar 114 is generally parallel to the occlusal surface 144. The bracket slot 130 is preferably positioned on the "F.A." point of the tooth, which is the midpoint of the crown 142 along the long axis.

When the bracket 100 is mounted on either a patient's upper or lower teeth, it is oriented such that the horizontal bar 114 is near the occlusal surface of the tooth and the vertical bar 112 extends gingivally from the horizontal bar 114.

The vertical and horizontal bars 112 and 114 may be perpendicular to each other. However, the angle between the bars 112 and 114 may be varied from 90° to accommodate teeth having occlusal surfaces that are not perpendicular to the tooth's long axis. In this case, use of a modified bracket is preferred so that the vertical bar 112 is aligned with the tooth's long axis and the horizontal bar 114 is parallel to the tooth's occlusal surface.

Because the bracket 100 can be oriented on a tooth by aligning the vertical bar 112 with the long axis of the tooth, placement of the bracket 100 on a tooth is easy compared to many conventional brackets. Consequently, fewer brackets will be placed improperly, reducing the need for arch wire bending to compensate for improper bracket placement. With fewer bends in the arch wire, the wire can slide through the brackets more easily, enabling more effective space closure.

As shown in FIGS. 12A and 13, an arch wire 146 is positioned in the slots 130 in each of the brackets 100. Preferably, the arch wire slot 130 has a rectangular or square cross section and the arch wire 146 has a complementary cross section. Also, an elastic o-ring 148 is coupled with each of the brackets 100 to hold the arch wire 146 in place. Although not shown, the o-ring 148 may be replaced by a ligature wire or other fastening member or an elastic chain or other force transmitting member.

FIGS. 12A, 12B and 12C illustrate some of the advantages of the bracket 100. First, because the vertical bar 112 is narrow and the slot 130 is small relative to the rest of the bracket 100 and the crown 142, the inter-bracket distance between the slots 130 of adjacent brackets 100 is large. A large inter-bracket distance is advantageous as it increases the span of the arch wire 146, thereby enhancing its flexibility and allowing greater control of the forces exerted by the arch wire. With larger inter-bracket distances a practitioner can advantageously use Neosentalloy for the arch wire in both the initial and finishing stages of treatment. With conventional brackets, Neosentalloy wire can usually be used during the initial stages of treatment and followed with use of a stainless steel wire.

The reduced width of the slot 130 is also advantageous as it reduces friction between the wire 146 and the bracket 100 during tooth movement. In particular, with bracket slots on posterior teeth, resistance to wire movement resulting from rotational forces at the mesiobuccal and distolingual areas of the slots is reduced. Similarly, resistance from tipping forces at the mesio-occlusal and distogingival areas of posterior bracket slots is reduced. Any torsional resistance at other contact areas of the slots is also reduced.

As shown in FIG. 13, after the arch wire 146 is positioned in the slot 130, the o-ring 148 is secured to the bracket 100 beneath the tie-wings 132 and 134 and over the arch wire 146 to form a general triangular shaped configuration. The arch wire 146 is thereby secured to the bracket 100.

FIG. 13 illustrates additional advantages of the bracket 100. First, because of the configuration of the bracket 100, the o-ring 148 forms a generally triangular or delta shape when in place over the arch wire 146. The o-ring 148 contacts the arch wire 146 near the base of this triangular shape at contact points 150, which are relatively widely spaced apart and generally located over contact points 125.

Contact points 125 identify where the arch wire 146 contacts bracket 100 during corrective rotational force applied to a misaligned tooth. The ratio of the distance between the wire engaging points 125 to the length of the slot 130 is approximately 3.5:1. The large spacing between contact points 125 allowed by the wide triangular shaped bracket enables the bracket 100 to develop sufficiently large moments for proper rotational control of the tooth. Because forces applied to a tooth during tooth movement are applied at the surface of the tooth through the bracket 100 rather than at the tooth's center of resistance, the tooth develops a tendency to rotate. The contact of the arch wire 146 at contact points 125 and held by the o-ring 148 provides sufficiently large corrective moments to enhance tooth rotation control because of the large rotational moment as seen in FIG. 12B. In addition, it should be noted that the bracket 100 can be used with an arch wire to apply corrective forces to straighten teeth that are initially spaced as shown in FIG. 12C. Then it is noted that the shortened distance between brackets provided by the wide horizontal bar of bracket 100 tends to prevent undesired rotation and provide movement along the direction of the arch wire.

When the arch wire 146 is initially positioned in the slot 130, it may be parallel to and slightly above the horizontal bar 114 as shown in FIG. 13. During use, tipping of the tooth may occur as the forces applied to the tooth are applied on the crown of the tooth and not on the tooth's center of resistance. The bracket 100, however, inhibits tipping by the contact between the arch wire 146 and one of the wire engaging points 125, which creates sufficiently large moments to deter the tipping. On posterior teeth, tip control reduces mesial tipping of the teeth in extraction sites and thereby reduces the risk of lateral open bites during closure.

Application of Orthodontic Brackets for Treatment of Orthodontosis

The previously described bracket system of the present invention is particularly well suited to the treatment of the various classifications of Orthodontosis. While other bracket systems may be used in accordance with the methods of the present invention, the bracket system described herein is preferred.

Localized Orthodontosis

For example, with regard to the treatment of localized orthodontosis (See FIGS. 3A-5B), the orthodontic brackets 18 may initially be applied only on teeth with localized orthodontosis of the alveolar bone. FIG. 4 depicts an example of a localized orthodontosis situation where a portion 14 of the alveolar bone 15 appears to be concave (i.e., deficient) by the lateral incisors 19 instead of convex or in front of the central incisors 16. As described above, the orthodontic appliances or brackets 18 are attached to the misaligned lateral incisors 19. Preferably, the brackets 18 are similar to and in accordance with the brackets 100 described previously and shown in FIGS. 9-13. An arch wire 17, preferably having a rectangular or square cross section, is connected to anchor brackets 24 attached to teeth on opposing sides of the lateral incisors 19 in order that corrective forces may be applied to the bracket 18 through the arch wire 17. The arch wire 17 is configured in the slot of each bracket 18 and corrective force is applied to torque the roots of the lateral incisors 19 causing the alveolar bone 15 above these roots to remodel more labially, restoring the bone morphology as each tooth is straighten. As the alveolar bone 15 gradually fills the previous area of deficiency 14, the localized orthodontosis is alleviated resulting in an elimination of a primary cause of the orthodontitis.

Similarly, FIG. 5A depicts another occurrence of localized orthodontosis where a portion 14 of the alveolar bone 15 exhibits a concave appearance or deficiency 14 from the improperly erupted lower first premolars 21 more lingually. Similarly as described above, and shown in FIG. 5A, the method of the present invention uses orthodontic appliances or brackets 18 attached to certain misaligned teeth which cause root movement, as opposed to tilting of the crown, with a single rectangular or square wire 17. Preferably, the brackets 18 are similar to and in accordance with the brackets 100 described previously and shown in FIGS. 9-13. An arch wire 17, preferably having a rectangular or square cross section, is connected to anchor brackets 24 attached to teeth on opposing sides of the premolars 21 in order that corrective forces may be applied to the brackets 18 through the arch wire 17. The arch wire 17 is configured in a slot of each bracket 18 and corrective force is applied to torque the roots of the premolars 21 causing the alveolar bone 15 above these roots to remodel more labially, restoring the bone morphology as each tooth is straightened. The movement of the root causes orthoeruption on the tooth root which serves to restore the alveolar bone 15. Thus, as shown in FIG. 5B, the alveolar bone 15 is restored on the root of the premolar tooth 21 which was moved into position from orthoeruption.

Premaxillary Orthodontosis

Figure 6A:
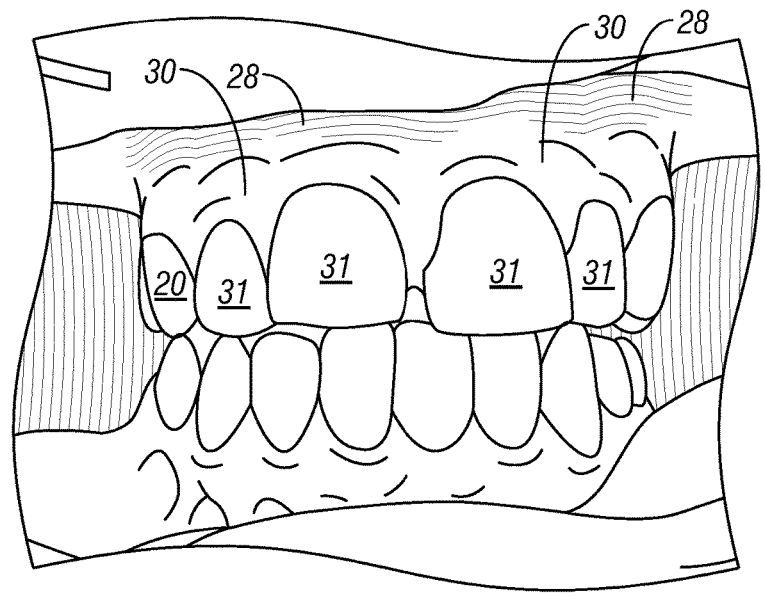
FIG. 6A depicts a frontal view of another example of a Class B Malocclusion (i.e., premaxillary orthodontosis) in accordance with the classification system of the present invention, that exhibits non-inflammatory (boney defect) deficiency of the alveolar bone from canine to canine in the upper area and excessive overjet.
Figure 6B:
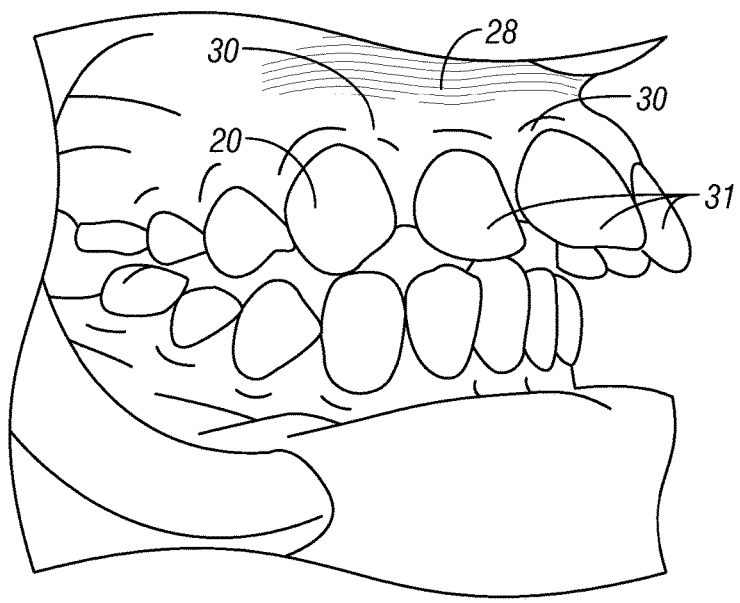
FIG. 6B depicts a perspective side view of the example of Class B Malocclusions (i.e., premaxillary orthodontosis) in FIG. 6A.
Figure 6C:
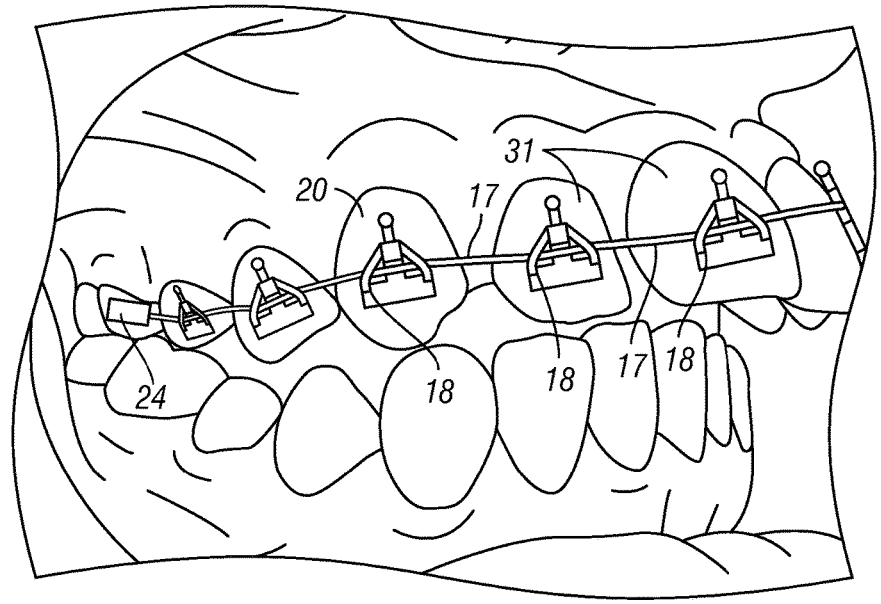
FIG. 6C depicts a perspective side view of the treatment of the example of a Class B Malocclusion (i.e., premaxillary orthodontosis) shown in FIG. 6A in accordance with the method of the present invention.
Figure 6D:
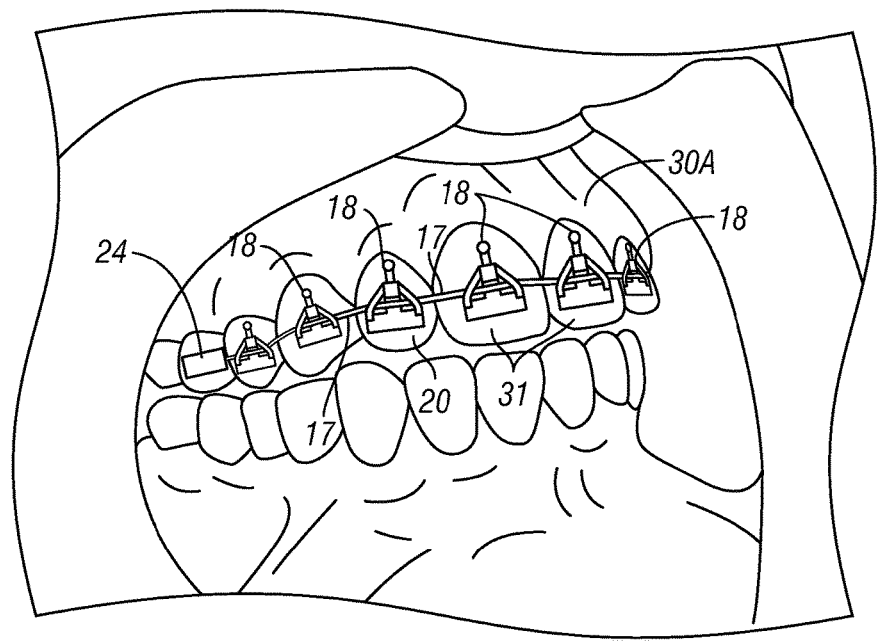
FIG. 6D depicts another perspective side view of the treatment of the example of a Class B Malocclusion (i.e., premaxillary orthodontosis) shown in FIG. 6A in accordance with the method of the present invention.

With regard to the treatment of premaxillary orthodontosis, FIGS. 6A-6B depicts a deficiency 28 of the alveolar bone 30 morphology by the upper anterior teeth (i.e., canines 20 and incisors 31), which can be restored after the roots are orthoerupted into an upright position. As shown in FIGS. 6C and 6D and described previously, orthodontic appliances or brackets 18 are attached to the misaligned upper anterior teeth (20, 31). Preferably, the brackets 18 are similar to and in accordance with the brackets 100 described previously and shown in FIGS. 9-13. An arch wire 17, preferably having a rectangular or square cross section, is connected to anchor brackets 24 attached to teeth on opposing sides of the upper anterior teeth so that corrective forces may be applied to the brackets 18 on the upper anterior teeth (20, 31) through the arch wire 17. The arch wire 17 is inserted into a slot configured in each bracket 18 and corrective force is applied to torque the roots of the upper anterior teeth (20, 31) causing the alveolar bone 30 above these roots to remodel more labially, restoring the bone morphology as each tooth is straightened.

Figure 7:
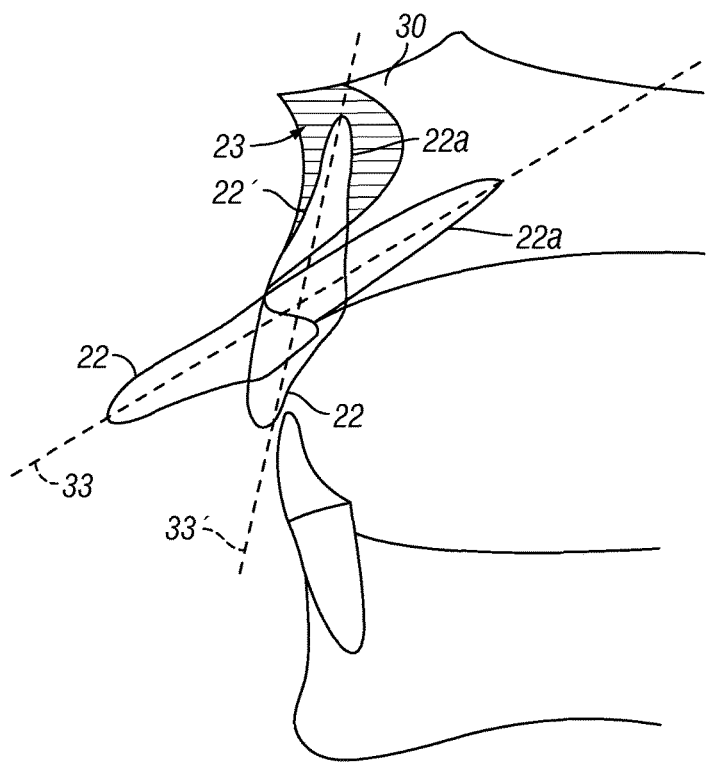
FIG. 7 illustrates the movement of the teeth in FIGS. 6A-E from their initial to final position.

Additionally, upper interproximal enamel reduction of the width of one or more of the upper teeth may also be combined with the attachment of the orthodontic appliances or brackets 18 as described above, molar to molar, to easily help alleviate this condition and restore the alveolar bone 30 to a proper level by creating spaces between the upper teeth and subsequently closing these spaces by uprighting the upper teeth into these spaces. In either case, as shown in FIG. 7, corrective force is applied to torque the roots so that the initial tooth axis 33 is gradually restored to a more upright configuration 33'. Uprighting the root 22a of the misaligned tooth 22 causes restoration of the alveolar bone 30 about the root 22a of the tooth 22 and eliminates the depression in the gums 23. By restoring the alveolar bone 30 the premaxillary orthodontosis is alleviated so that the underlying cause of the orthodontitis is eliminated.

Figure 6E:
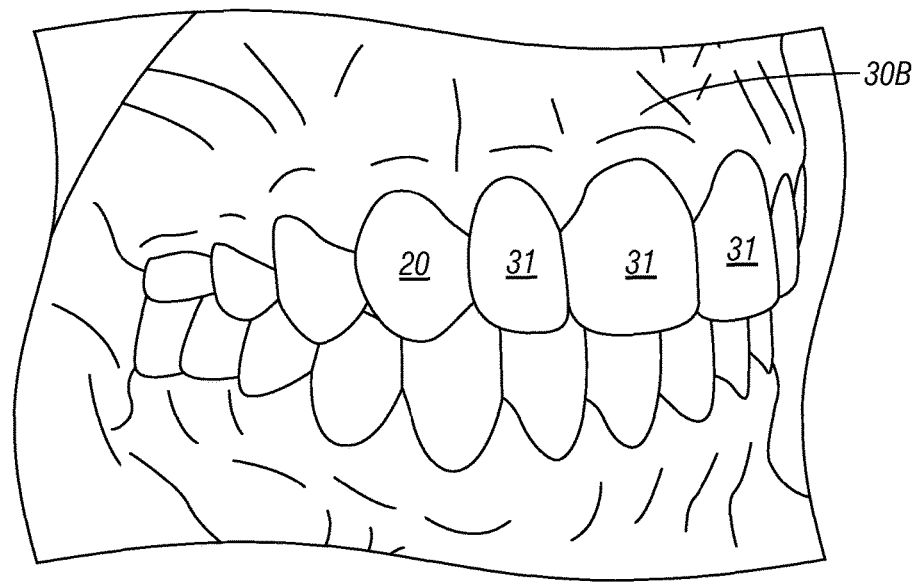
FIG. 6E depicts perspective view of the Class B Malocclusion (i.e., premaxillary orthodontosis) shown in FIG. 6A corrected to a proper occlusion utilizing the method of the present invention.

FIG. 6D depicts a partially restored and remodeled of the alveolar bone 30A during the course of the method of treatment. As the alveolar bone 30A gradually fills the previous area of deficiency 28 the premaxillary orthodontosis is alleviated resulting in an elimination of a primary cause of the orthodontitis. FIG. 6E depicts the alveolar bone 30 successfully restored following the treatment method of the present invention. The alveolar bone 30B morphology no longer displays any deficiencies and the upper anterior teeth (20, 31) have all been uprighted. The nonextraction therapy method of the present invention restores the mouth to its natural dental arches as if the teeth erupted normally to these positions in the first place. However, if the patient also demonstrates mandibular retrognathia, then a surgical procedure may also be indicated.

Mandibular Orthodontosis

With regard to the treatment of mandibular orthodontosis, FIG. 8A depicts an alveolar bone 40 having an excess of inward or lingual axis tilt morphology in the teeth of the lower jaw. These types of cases typically demonstrate minimal overbite/overjet with retroclined lower incisors or negative overjet (i.e., underbite). These cases show excess alveolar bone 40 and/or basal bone formation with retroclined incisors 36 (i.e., a condition wherein the tooth axes 42 are inclined backwards).

Figure 8C:
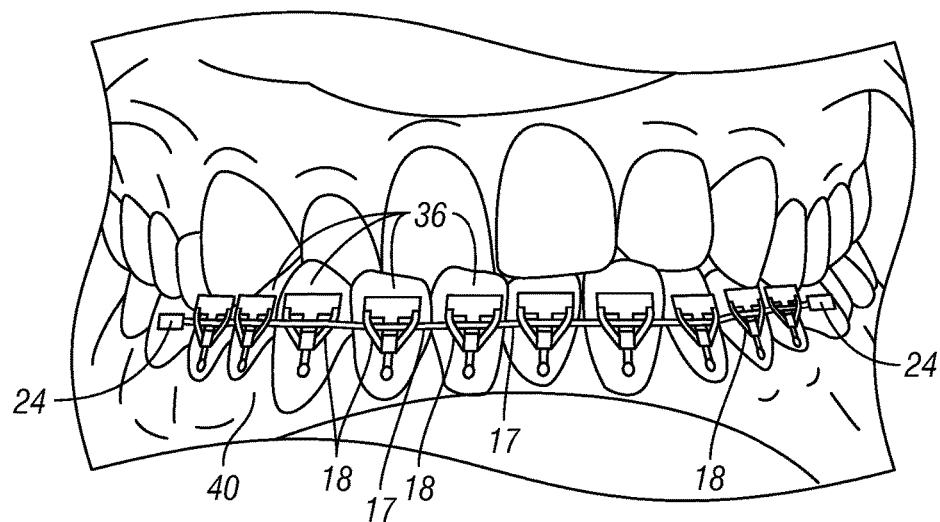
FIG. 8C depicts a frontal view of the treatment of the Class C Malocclusion (i.e., mandibular orthodontosis) shown in FIGS. 8A-B in accordance with the method of the present invention.
Figure 8D:
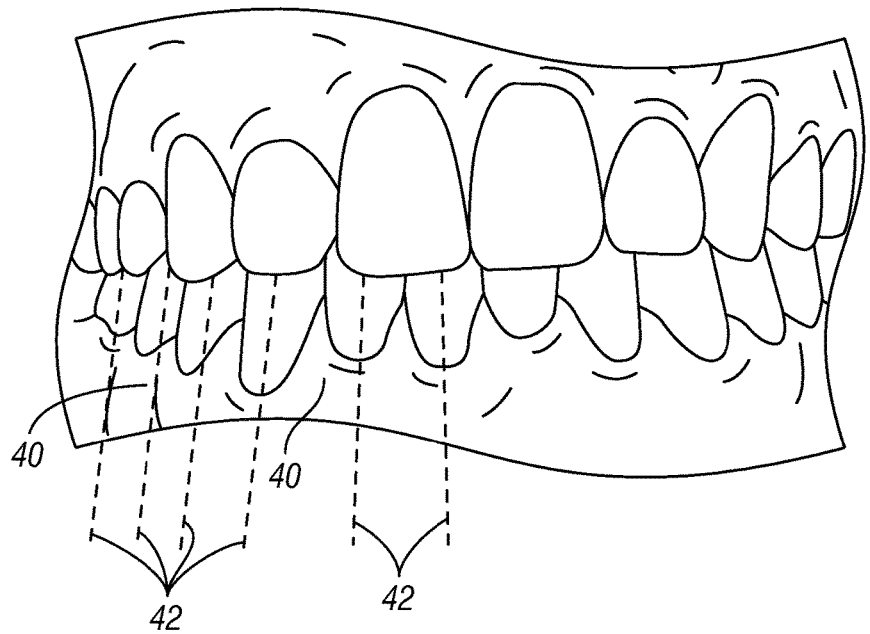
FIG. 8D depicts the view of the Class C Malocclusion (i.e., mandibular orthodontosis) shown in FIG. 8A uprighted to a proper occlusion utilizing the method of the present invention.

As shown in FIG. 8B, the lower interproximal enamel reduction of the width of one or more of the lower teeth combined with the attachment of the orthodontic appliances or brackets 18 as described above, molar 50A to molar 50B, are used to alleviate this condition for up to three lower anterior teeth in underbite relation. Preferably, the brackets 18 are similar to and in accordance with the brackets 100 described previously and shown in FIGS. 9-13. As shown in FIG. 8C, an arch wire 17, preferably having a rectangular or square cross section, is connected to anchor brackets 24 attached to teeth on opposing sides of the retroclined incisors 36 in order to apply corrective forces to the brackets 18 on the retroclined incisors 36 through the arch wire 17. The arch wire 17 is inserted into a slot configured in each bracket 18 and corrective force is applied to torque the roots of the retroclined incisors 36 causing the alveolar bone 40 below these roots to remodel more lingually, restoring the bone morphology as each tooth is straightened. Thus, as shown in FIG. 8D the alveolar bone 40 is restored to a proper level by creating spaces 25 between the lower teeth and subsequently closing these spaces 25 by uprighting the lower teeth into these spaces 25 using the brackets 18 described above. If more teeth are in anterior crossbite then a surgical procedure may also be indicated. FIG. 8D depicts the alveolar bone 40 previously exhibiting mandibular orthodontosis successfully restored following the treatment of the present invention. The lingual axis tilt of the lower teeth axes 42 is corrected by uprighting the selected teeth, resulting in the alveolar bone 40 being restored.

The orthodontic bracket system of the present invention delivers very light forces to simulate the low force eruption stimuli that is needed to allow for bone remodeling around the displaced roots area of the alveolar bone and thus achieve correction of root position. The nonextraction therapy is achieved through bone remodeling from root movement initiated at the onset of orthodontic treatment that results in the orthoeruption of teeth.

In all depicted cases, once the root is uprighted by the orthodontic bracket system of the present invention, the alveolar bone is restored and a primary cause of the orthodontitis (i.e., the gingivitis from malpositioned teeth) is alleviated.

It will now be evident to those skilled in the art that there has been described herein an improved orthodontic classification and diagnosis system and method for treating orthodontitis. Although the invention hereof has been described by way of a preferred embodiment, it will be evident that other adaptations and modifications can be employed without departing from the spirit and scope thereof. The terms and expressions employed herein have been used as terms of description and not of limitation; and thus, there is no intent of excluding equivalents, but on the contrary it is intended to cover any and all equivalents that may be employed without departing from the spirit and scope of the invention.

I claim:

1. A method for treating and alleviating orthodontitis in an affected area of a patient, the method comprising the steps of:

analyzing the morphology, appearance and contour of the patient's alveolar bone and ridge by evaluating the alveolar bone and roots in the horizontal dimension;

classifying a naturally occurring non-inflammatory improper morphology of the patient's alveolar bone as at least one of the following:

a) localized orthodontosis comprising a deficiency of the alveolor bone at a specific location in the horizontal dimension;

b) premaxillary orthodontosis comprising a deficiency of the alveolar bone in the patient's premaxilla resulting in flared upper anterior teeth and an underdeveloped premaxilla caused by roots of the upper anterior teeth not erupting to their full upright potential; or c) mandibular orthodontosis comprising excess alveolar bone and/or basal bone formation with retroclined incisors;

applying an orthodontic bracket to a tooth in the affected area, the bracket having a substantially vertical element having a slot formed therein for receiving an arch wire, and a substantially horizontal element connected to the vertical element with the vertical element being positioned gingivally with respect to the horizontal element, the horizontal element having opposing first and second ends extending away from the vertical element and defining a pair of spaced-apart wire engaging points engageable with the arch wire for enabling proper rotational control of the bracket during use, the slot in the vertical element being vertically spaced apart from the horizontal element to limit contact between the arch wire and the horizontal element and wherein the ratio of the distance between the wire engaging points to the length of the slot is approximately 3.5:1;

installing the arch wire within the slot in the bracket;

attaching a force transmitting member to the bracket for applying a force to the bracket initially causing the crown of the tooth to tilt relative to a vertical axis through the tooth and thereby causing the arch wire to contact one of the wire engaging points and a part of the vertical element defining an upper portion of the slot that is distal to the one wire engaging point such that further force applied by the force transmitting member causes a reverse tilt of the root of the tooth relative to the vertical axis, and correcting the position of the tooth by uprighting the roots of the tooth, thereby restoring said patient's alveolar bone morphology and alleviating orthodontitis in the affected area.

2. The method of claim 1 wherein said improper morphology of the patient's alveolar bone comprises a deficiency in the alveolar bone comprising localized orthodontosis.

3. The method of claim 1 wherein said improper morphology of the patient's alveolar bone comprises a deficiency in the alveolar bone comprising premaxillary orthodontosis.

4. The method of claim 3 wherein restoring said improper morphology of the patient's alveolar bone further comprises interproximal enamel reduction of the width of at least one of the upper teeth, molar to molar, creating at least one space between the upper teeth and subsequently closing said at least one space by uprighting the upper teeth.

5. The method of claim 1 wherein said improper morphology of the patient's alveolar bone comprises an excess of alveolar bone comprising mandibular orthodontitis.

6. The method of claim 5 wherein restoring said excess of alveolar bone further comprises interproximal enamel reduction of the width of at least one of the lower teeth, molar to molar, creating at least one space between the lower teeth and subsequently closing said at least one space by uprighting the lower teeth.

7. The method of claim 1 wherein the bracket is triangular shaped.

8. The method of claim 7 wherein the bracket is provided with a horizontal element having a width of between 60-90% of the width of the tooth.

9. The method of claim 8 wherein said horizontal element has a width of between 65-85% of the width of the tooth.

10. A method for restoring an improper morphology of alveolar bone around a tooth in a patient, using an orthodontic bracket with an arch wire, the method comprising:
1) analyzing the appearance and contour of the patient's alveolar bone and ridge by evaluating the alveolar bone and roots in the horizontal dimension;
2) classifying naturally occurring malocclusions in the patient's teeth as at least one of the following:
   a. localized orthodontosis comprising a deficiency of the alveolor bone at a specific location in the horizontal dimension;
   b. premaxillary orthodontosis comprising a deficiency of the alveolar bone in the patient's premaxilla; or
   c. mandibular orthodontosis comprising excess alveolar bone and/or basal bone formation with retroclined incisors;
3) applying the bracket to the tooth;
4) installing the arch wire within a slot in the bracket; and
5) applying a force to the bracket by attaching a force transmitting member to the bracket, initiating a mechanical stimulus on a root of the tooth inducing the tooth to move along an eruption path that uprights the root of the tooth causing orthoeruption, which corrects the position of the tooth and restores said morphology of said alveolar bone.

11. A method for treating and alleviating orthodontitis in an affected area of a patient, comprising:

1) classifying naturally occurring malocclusions of a patient's malpositioned teeth by analyzing the appearance and contour of the patient's alveolar bone and ridge by evaluating the patient's alveolar bone and roots in the horizontal dimension, and assigning at least one of the following classifications:
   a. localized orthodontosis comprising a deficiency of the alveolar bone at a specific location in the horizontal dimension;
   b. premaxillary orthodontosis comprising a deficiency of the alveolar bone in the patient's premaxilla; or
   c. mandibular orthodontosis comprising excess alveolar bone and/or basal bone formation with retroclined incisors;
2) alleviating said orthodontitis by restoring said deficiency or excess of the alveolar bone in the affected area by uprighting the roots of the patient's malpositioned teeth by:
   a. applying an orthodontic bracket to one of the patient's malpositioned teeth, the bracket having a substantially vertical element having a slot formed therein for receiving an arch wire, and a substantially horizontal element connected to the vertical element with the vertical element being positioned gingivally with respect to the horizontal element, the horizontal element having opposing first and second ends extending away from the vertical element and defining a pair of spaced-apart wire engaging points engageable with an arch wire for enabling proper rotational control of the bracket during use, the slot in the vertical element being vertically spaced apart from the horizontal element to limit contact between the arch wire and the horizontal element and wherein the ratio of the distance between the wire engaging points to the length of the slot is approximately 3.5:1;
   b. installing the arch wire within the slot in the bracket; and
   c. attaching a force transmitting member to the bracket for applying a force to the bracket initially causing the crown of the tooth to tilt relative to a vertical axis through the tooth and thereby causing the arch wire to contact one of the wire engaging points and a part of the vertical element defining an upper portion of the slot that is distal to the one wire engaging point such that further force applied by the force transmitting member causes a reverse tilt of the root of the tooth relative to the vertical axis, thereby restoring the alveolar bone by correcting the position of the tooth.

12. The method of claim 11 wherein said classification of the patient's alveolar bone comprises premaxillary orthodontosis and wherein restoring said deficiency of alveolar bone further comprises interproximal enamel reduction of the width of at least one of the upper teeth, molar to molar, creating at least one space between the upper teeth and subsequently closing said at least one space by uprighting the upper teeth.

13. The method of claim 11 wherein said classification of the patient's alveolar bone comprises mandibular orthodontosis and wherein restoring said excess of alveolar bone further comprises interproximal enamel reduction of the width of at least one of the lower teeth, molar to molar, creating at least one space between the lower teeth and subsequently closing said at least one space by uprighting the lower teeth.

14. The method of claim 11 wherein the bracket is triangular shaped.

15. The method of claim 14 wherein the bracket is provided with a horizontal element having a width of between 60-90% of the width of the tooth.

16. The method of claim 14 wherein said horizontal element has a width of between 65-85% of the width of the tooth.

17. The method of claim 14 wherein the slot formed in the orthodontic bracket is elevated above the horizontal element.

18. The method of claim 17 wherein the slot has a rectangular cross section and the arch wire has a complementary cross section.

19. The method of claim 14 wherein the arch wire has a square cross section.

* * * * *